(12) United States Patent
Karwoski et al.

(10) Patent No.: US 7,628,795 B2
(45) Date of Patent: *Dec. 8, 2009

(54) TUNNELING DEVICE FOR USE WITH A GRAFT

(75) Inventors: Theodore Karwoski, Hollis, NH (US); Mark D. Avella, Londonderry, NH (US)

(73) Assignee: Atrium Medical Corporation, Hudson, NH (US)

( * ) Notice: Subject to any disclaimer, the term of this patent is extended or adjusted under 35 U.S.C. 154(b) by 754 days.

This patent is subject to a terminal disclaimer.

(21) Appl. No.: 10/442,482

(22) Filed: May 20, 2003

(65) Prior Publication Data

US 2006/0173467 A1    Aug. 3, 2006

Related U.S. Application Data

(63) Continuation-in-part of application No. 08/937,083, filed on Sep. 24, 1997, now Pat. No. 6,565,594.

(51) Int. Cl.
*A61F 11/00* (2006.01)
(52) U.S. Cl. .................... 606/108; 623/11.11
(58) Field of Classification Search ........ 606/1, 606/108; 623/1.1, 1.11, 1.12, 1.23, 13.11–13.15; *A61F 2/06*

See application file for complete search history.

(56) References Cited

U.S. PATENT DOCUMENTS

| | | |
|---|---|---|
| 2,836,181 A | 5/1958 | Tapp |
| 3,981,299 A | 9/1976 | Murray |
| 4,574,806 A | 3/1986 | McCarthy |
| 4,733,665 A | 3/1988 | Palmaz |
| 4,739,762 A | 4/1988 | Palmaz |
| 4,775,380 A | 10/1988 | Seedhom et al. |
| 4,776,337 A | 10/1988 | Palmaz |

(Continued)

FOREIGN PATENT DOCUMENTS

EP    0515007 B1    11/1992

(Continued)

OTHER PUBLICATIONS

Brochure: Atrium Hybrid PTFE, Vascular Grafts Product Catalog, 1995.

(Continued)

*Primary Examiner*—Corrine M McDermott
*Assistant Examiner*—Jason-Dennis Stewart
(74) *Attorney, Agent, or Firm*—Lahive & Cockfield, LLP; Kevin J. Canning

(57) ABSTRACT

A tunneling device is provided for implanting a natural tissue vascular graft in a body. The tunneling device may include a flexible sheath to assist in locating the vascular graft in the body. According to one example, a connector having a longitudinal coupler, such as a surgical tie, may be used to locate the natural tissue graft within the sheath. The natural tissue graft can be secured to the surgical tie when the sheath is retracted. Before tunneling, the sheath can be extended to cover the natural tissue graft to protect the natural tissue graft from damage and aid in locating the natural tissue graft in the body. When the natural tissue graft is positioned as desired in the body, the sheath is removed.

14 Claims, 7 Drawing Sheets

U.S. PATENT DOCUMENTS

| | | |
|---|---|---|
| 4,846,191 A | 7/1989 | Brockway et al. |
| 5,122,154 A | 6/1992 | Rhodes |
| 5,234,438 A | 8/1993 | Semrad |
| 5,246,452 A | 9/1993 | Sinnott |
| 5,269,755 A | 12/1993 | Bodicky |
| 5,290,295 A * | 3/1994 | Querals et al. .............. 623/1.23 |
| 5,306,240 A | 4/1994 | Berry |
| 5,370,610 A | 12/1994 | Reynolds |
| 5,393,302 A | 2/1995 | Clark et al. |
| 5,443,499 A | 8/1995 | Schmitt |
| 5,474,824 A | 12/1995 | Martakos et al. |
| 5,607,443 A | 3/1997 | Kieturakis et al. |
| 5,662,703 A * | 9/1997 | Yurek et al. ................ 623/1.12 |
| 5,797,920 A * | 8/1998 | Kim ........................... 606/108 |
| 5,804,318 A | 9/1998 | Pinchuk et al. |
| 6,090,107 A * | 7/2000 | Borgmeier et al. ............ 606/41 |
| 6,488,701 B1 * | 12/2002 | Nolting et al. ............. 623/1.13 |

FOREIGN PATENT DOCUMENTS

| | | |
|---|---|---|
| WO | WO-95/05131 A1 | 2/1995 |
| WO | WO-95/05132 A1 | 2/1995 |
| WO | WO-96/00103 A1 | 1/1996 |
| WO | WO-96/28115 A1 | 9/1996 |

OTHER PUBLICATIONS

Brochure: IMPRA Kelly-Wick Access Tunneler Set KW2000, 1989.
Brochure: The Gore Tunneler, 1995.
Brochure: Scanlan Vascular Tunneler System, 1993.
IMPRA Technical Report (TR-106), Angioaccess Tunneling, 1993.

* cited by examiner

TUNNELING DEVICE FOR USE WITH A GRAFT

REFERENCE TO RELATED APPLICATIONS

This application claims priority to and is a continuation-in-part of U.S. patent application Ser. No. 08/937,083, now U.S. Pat. No. 6,565,594 originally filed Sep. 24, 1997, a Continuation Prosecution Application (CPA) application of which was filed Jun. 14, 2000, entitled Tunneling Device, pending, the contents of which are herein incorporated by reference.

FIELD OF THE INVENTION

This invention relates generally to tunneling devices for locating a graft in the body, and more specifically to tunneling devices that include a flexible sheath to protect the device during the handling and implantation of the graft in the body.

BACKGROUND OF THE INVENTION

It is commonly known that cardiac bypass surgery is a means to divert the flow of blood around arteries or veins that have become occluded or stenosed, and thus eliminate an impediment to the requirement of blood flow. A vascular graft which is a tubular device that is suitable for implantation in the body is used to reestablish or redirect the flow of blood beyond the blockage area. Surgical implantation procedures require placement of the vascular graft within the subcutaneous tissue. Vascular graft implantation requires the creation of an anatomic or subcutaneous pathway commonly called a graft tunnel. Tunneling is a required surgical step in the vascular bypass procedure for all peripheral, vascular access and extra anatomical graft locations which result in localized dissection injury to tissue. The tunnel diameter relative to the implant diameter, as well as the abrasive force exerted by the implant during insertion have a significant impact on the resultant trauma to this tissue and its healing response to both the blunt dissection of the tunnel space tissue and the vascular graft material.

It is advantageous in the clinical setting to minimize trauma to this tissue through the use of an improved tunneling technique and implant device. The conventional approach to creating a graft tunnel or space for the vascular graft is with the use of a rigid rod like device called a graft tunneler or tunneler instrument. Tunneler instruments come in varying sizes. They are usually very bulky, and require cleaning and sterilization before reuse. Improper size selection of the tunneler instrument or improper tunneling technique may result in a larger than required tunnel path through the tissue. An example of a tunneler instrument which has been designed to minimize the problem of oversizing a tissue tunnel is the Kelly-Wick tunneling set from Bard® Impra®, which is specifically designed for the implantation of vascular grafts without a tunnel sheath. Hence, this instrument is a "sheathless" system that draws a vascular graft through the dissected tissue tunnel which is created by a insertion of a rigid, bullet tipped rod through a skin incision, and forced horizontally through the subcutaneous tissue.

These type of tunneler instruments are reusable but expensive, and consequently hospitals often maintain only a limited supply of these instruments for operating room use. Since these instruments are reusable, they must be cleaned, packaged and resterilized between use. Frequently in emergency vascular surgery situations, the proper sized tunneling tip, whether it be a specific diameter, length or size, is not readily available. Consequently, the surgeon is forced to use an improper sized bullet tip (not matched to the outside diameter of the implant), or use a make-shift device. This may result in the creation of a vascular graft tunnel that is too large or too small for the graft, causing unnecessary or increased patient complications. If the tunneler instrument used creates a tunnel track that is too large for the size vascular graft being implanted, the tubular graft will not fit snugly within the tunnel and large "tunnel spaces" will exit along the entire length of the graft. This event is considered to be a major contributor to postoperative graft complications such as wound inflammation, graft material infection, and or seroma formation about the outside space of implanted graft. With an improper or "over-sized" tunnel, a significant amount of blood may pool and collect around the entire length of the implant, causing postoperative graft failure due to poor healing of the localized tissue, graft infection, and painful tissue swelling due to fluid accumulation between the dissected tissue and the implant.

Using a tunneler instrument to create a tunnel for the insertion and implantation of the vascular graft, the rigid rod like device is forcefully passed through the subcutaneous tissue horizontally between two surgically prepared incisions, until the bullet tip end is exposed at the second incision or exit wound. Once this tunneler tip is exposed, the tubular vascular graft material is placed over the bullet tipped device and tied onto the end of the indwelling tunneler rod tip with a sterile suture thread. The surgeon must carefully tie the graft to the tunneler rod with several suture knots, so as to avoid the graft from slipping off of the tunneler tip when pulled beneath the skin and into the implant position. After the vascular graft has been pulled through the dissected tissue cavity into final position, the vascular graft is then cut free at the tied end of the tunneler rod. Since the graft is exposed to the operative wound during attachment and insertion of the graft, the sterility and purity of the graft material are compromised. The process of suturing the graft to the tunneler rod and the manipulation of the graft by the surgeon further compromise the sterility of the device as a result of this "hands on" contact. Handling of the graft material during a tunneling procedure by contact with the nurse's and surgeon's gloves also increases the risk of infection by contamination from glove contact and operative wound/skin surface contact.

Another source of tissue trauma and postoperative graft complications can be created by the graft material itself due to the way the surgeon ties the graft to the tunneler. If not carefully prepared by the surgeon, part of the graft material may freely protrude over the tunneler instrument rod, forming a lip of free graft material in front of the suture tie. When the graft is forcibly pulled into and through the dissected tissue tunnel, such pulling action causes this graft material to compress, bunch up and create an abrupt or raised area in front of the suture tie which bluntly plows through the tissue, increasing the diameter of the tunnel and effectively increasing the amount of device drag in an abrasive manner, further traumatizing tissue along the entire tunnel track. This plowing action not only increases the potential for even more undesirable bleeding and tunnel track inflammation, but makes more work for the surgeon during graft insertion, particularly during long peripheral and extra anatomical bypass. This forceful graft insertion technique and risk of patient complications occurs with all commercially available vascular grafts when used with "sheathless" tunneler instruments.

"Pre-wetting" of the vascular graft material is another undesirable complication that occurs with traditional sheathless tunnelers. Since artificial vascular grafts are constructed from porous biomaterials designed to encourage rapid cell ingrowth following implantation, for example vascular grafts made from expanded polytetrafluoroethylene (PTFE), it is known that microporous graft materials should not be "pre-wetted" or "presoaked" with blood. These conditions lead to fluid leakage through the graft material once blood flow is restored within the implant, much the way a canvas tent would leak in a rain storm. If, during insertion of the graft with a traditional sheathless tunneler instrument, the tunneler tip is undersized in comparison to the outside diameter of the graft being implanted, the leading 2-5 cm length of graft material will become completely saturated with blood during the process of dragging the graft through the tissue. This is caused by the pressure placed on the tissue during graft insertion due to the initial under-sized tunnel tract. Since the thickness of the graft material adds to the outer diameter of the original bullet tip outer diameter, the leading edge of the graft material is forcibly dragged through the bleeding tissue. The pressure on the graft is controlled by the size of the tunneler tip which bluntly dissected the original tunnel space. The amount of pressure placed on the adjacent bleeding tissue and onto the graft material varies according to surgical technique and tunneler tip size selection, and thus the length and amount of graft material saturation with blood varies from patient to patient. This accounts for why some vascular graft patients unpredictably develop "seroma" formation, a serious complication of fluid accumulation around all or part of the graft material, causing moderate pain, edema and swelling of the closed wound, interstitial edema and inflammation, poor healing of the implant material, graft thrombosis and the most critical of all, systemic infection, which has an unacceptable morbidity rate. Therefore, use of a sheathless tunneler technique is not without its risk of patient complications following surgery. Such vascular graft complications may not appear for up to 30 days after patient discharge from the hospital. Hence, any surgical technique with a sheathless tunneler device which could reduce these unpredictable postoperative conditions would be clinically significant and cost effective in today's world of managed care medicine.

One example of a popular "sheathless" tunneler is the Kelley-Wick tunneling set commercially available from Bard-Impra, Tempe, Ariz. This tunneler is a one piece rod, specifically designed for the implantation of peripheral, vascular grafts (non aortic, non coronary), whereby it is the desire of the surgeon to minimize the outer tunnel space around the vascular graft implant. The device is comprised of a rigid rod that is permanently connected to a knurled handle. The rod may vary in shape and size from a straight shaft to a semicircular shaft, allowing for a variety of surgical techniques and/or placement locations. The rod is fabricated from a rigid material such as stainless steel. The rod of the instrument may terminate with a threaded on bullet tip at the opposite end to the handle. The threaded rod and bullet tip facilitates the use of different size bullet tips with a single tunneler rod to create different size tissue channels or tunnels. The Kelly-Wick tunneler is manually forced through the tissue horizontally between two incisions by the surgeon to thereby create a bluntly dissected tunnel. When tunnel dissection is completed with the bullet tip end protruding out of the distal skin incision, the vascular graft to be implanted is then attached to the tunneler tip by pushing one end of the tubular graft over the bulbous end of the bullet tip, carefully suturing and tying the end of the graft material to the bullet tip with one or two sterile suture threads. Once tied to the tunneler instrument, the vascular graft is drawn into the subcutaneous tissue channel by pulling the tunneler rod out through the first skin incision until the graft is pulled completely into the patient. When appropriately positioned between the area being bypassed, the surgeon cleanly cuts the graft away from the sutured end of the tunneler rod and tip.

While the Kelly-Wick sheathless tunneler is a popular surgical device, it has all of the previously described disadvantages. This tunneler requires that the graft be surgically positioned by pulling the graft through bluntly dissected tissue, causing further abrasion due to surface friction between the outside surface of the graft and the tissue. Further, the graft is attached to the bullet tip by sliding the graft over the tip and tying the tip and graft together. The mating of the tip and graft in this fashion creates a square edged lip at the end of the graft which tends to compress and enlarge when the graft is pulled through the tunnel, creating a "plowing" effect and causing further abrasion to the tissue wall and a larger tunnel channel. Depending on the care and preparation of the suture tying technique by the surgeon, the tunnel cavity is sometimes enlarged so that the graft does not seat snugly in the tunnel and the extra space about the graft implant would likely fill with blood and interstitial fluid.

An alternative tunneling technique uses a two (2) part tunneler instrument called a rigid "sheath tunneler," which includes an oversized rigid metal or plastic hollow tube with a removable bullet shaped dissection tip on one end, and an internal smaller diameter indwelling rod for attaching the vascular graft material. The two part rigid sheath tunneler allows the surgeon to easily pull the vascular graft through the internal lumen of the rigid outer sheath, being substantially oversized in comparison to the outside diameter of the vascular graft. Once the graft has been pulled into the rigid sheath, the graft material is cut free from the "pull-through rod" and the subcutaneous rigid sheath is then extracted out from the tissue track and exit wound without extracting the graft. These rigid sheath tunnelers may at times be difficult to use since the rigid tubular sheaths are awkward to extract from the subcutaneous tissue due to the surface friction of the indwelling instrument. Sheath tunneler instruments require the surgeon to hold the graft in position with the pull-thru rod, a vascular clamp or gloved hands simultaneous to pulling on the rigid tubular sheath to remove it from the subcutaneous tissue.

An example of a "sheath" tunneler is the Gore tunneler which is produced by W. L. Gore and Associates, Inc. of Flagstaff, Ariz. This two part tunneler instrument is used to implant a vascular graft subcutaneously with an oversized tissue passageway. The Gore tunneler is comprised of a hollow rigid metal shaft connected to a handle with a removable bullet tip at one end of the shaft. The shaft is fabricated from stainless steel and fits into a formed handle with a center rod. The instrument is used to bluntly dissect a tunnel by forcing the bullet tipped hollow shaft through the tissue. After suture attachment of the graft material to the inner rod the vascular graft is then easily drawn through the entire length of the oversized hollow tube.

With the graft positioned in place, but still within the hollow shaft, the outer shaft tunneler must next be carefully extracted from the tissue tunnel without extracting the graft from the subcutaneous passageway. All rigid sheath tunneler devices may at times be difficult to extract from the tissue due to the compressive tension on the surrounding tissue and surface friction thereby created. The surgeon may find it necessary to use both hands to grasp the rigid hollow sheath, requiring an assistant to hold the vascular graft in position, hence, use of these type of instruments still may require significant surgical glove contact of the vascular graft during tunneling.

Another example of a two part rigid sheath tunneler is the "Scanlan" tunneler, which is similar in operative technique to the Gore device except that the rigid sheath is constructed of hard plastic and considered disposable (1 time use). The hollow shaft or tube is produced from a thicker walled, rigid plastic tube material in contrast to the thin walled stainless steel tube used with the Gore device. The Scanlan plastic hollow shaft includes a pressure fitted, removable bullet tip and an internal retractable rod. The surgeon forcibly passes the bullet shaped shaft tunneler through the tissue to create the tunnel. The bullet shaped tip of the plastic shaft is then removed and the vascular graft is attached to the inner rod with an alligator tip clamp located on the end of the pull-thru rod. Like the Gore tunneler, the Scanlan tunneler allows the graft to be easily drawn into and through the oversized hollow shaft. With two hands, the rigid plastic tube is carefully withdrawn out of the patient over the graft thru the proximal exit wound or skin incision, leaving the vascular graft within the tissue tunnel. The graft is then detached from the rod. Similar to the metal sheath tunneler instruments, the rigid plastic tube may also at times be difficult to extract from the tissue tunnel due to the compressive tension created by the bluntly dissected tissue and the surface friction created along the indwelling rigid walled shaft.

As has been previously noted, tunnelers are expensive, and consequently hospitals maintain only a limited supply of these surgical devices for hospital use. Most instruments are reusable, and are required to be washed and sterilized between use. It sometimes happens that in an emergency situation whereby disposable devices are employed, the proper sized disposable shaft component is not available. Therefore, surgeons are at times forced to use improper sized tunneling devices or alternative subcutaneous dissection items such as a gloved finger, or hemostat clamp, or a sharp surgical instrument such as a thoracic catheter trocar stylette. Thus, the resulting tunnel created by these alternative sized devices may create too large a tunnel for the vascular graft and/or unnecessary bleeding and trauma, placing the vascular implant and patient at risk.

SUMMARY OF THE INVENTION

Broadly speaking, the present invention provides for an implantable tunneling device capable of use with a graft, including, but not limited to, a natural tissue graft. In one exemplary embodiment of the invention a sheath may provide a flexible, compressible outer surface for a natural tissue graft that may allow for easier insertion of the graft into the tissue cavity with less trauma, less friction, less blunt dissection and less drag during placement. Due to the smoothness and collapsible low profile of the sheath, this tunneling device may be faster and easier to use, in addition to being less traumatic to tissue. This sheath device may be made more lubricious by the application of a wide variety of coatings.

In a further aspect of the invention, a tunneling device is realized as a vascular graft that is enclosed in a sheath for surrounding the graft during the implantation process. The thin collapsible sheath allows for easier insertion of the graft through the tissue cavity due to the unrestricted and flexible nature of the compressible outer surface. The pre-attached sheath may be coated on the outside surface with a lubricious substance to seek to provide a low coefficient of friction, aiding movement of the sheath and graft through tissue when pulled by a tunneler.

It is contemplated that the graft need not be completely implanted within the patient to be considered within the scope of the present invention.

An implantable vascular graft may be implanted with less surgical manipulation and less tissue trauma than with a traditional rigid sheath tunneler. More specifically, a tunnel diameter may be matched to the same outside diameter of the vascular graft.

It is also desirable to provide for a tunneling device that incorporates a thin compressible sheath to protect an enclosed graft without substantially increasing the outside diameter of the tunneling device. The thin compressible sheath is constructed of a smooth, flexible and easily compressive material for easy insertion within a tissue tunnel. A hydrophilic coating may also be applied to the sheath to increase its lubricousness to minimize tissue drag and tissue trauma during insertion of the implant or sheath removal after implant positioning.

According to one embodiment, a tunneling device for subcutaneous deployment by a tunneling instrument is provided. In this example, the tunneling device includes a sutureless connector adapted to couple a natural tissue graft to a tunneling instrument. A sheath is also included and is attached to the connector and adapted to cover a length of the natural tissue graft.

According to another embodiment of the invention, a tunneling device is provided having a sheath and a connector that is adapted to couple the tunneling instrument to the sheath. In this example, the connector includes a longitudinal coupler. A first end of the longitudinal coupler is located within a lumen of the sheath and the longitudinal coupler is adapted to be attached to a graft.

According to a further embodiment of the invention, a tunneling device has a natural tissue graft and a sutureless connector adapted to couple a tunneling instrument to the natural tissue graft by a compressive force on the natural tissue graft. In this example, a sheath is attached to the connector and is adapted to cover a length of the natural tissue graft.

Another embodiment provides a system for subcutaneously deploying a natural tissue graft in a patient. The system includes a tunneling instrument for use in a subcutaneous tissue cavity in the patient. A connector coupled to the tunneling instrument is provided to connect the natural tissue graft to the tunneling instrument. The natural tissue graft is mounted to the connector. A sheath is attached to and encloses at least one end and a portion of the length of the natural tissue graft.

BRIEF DESCRIPTION OF THE DRAWINGS

The present invention will become better understood with reference to the following description and accompanying drawings, wherein.

DETAILED DESCRIPTION OF THE ILLUSTRATED EMBODIMENT

Figure 1:
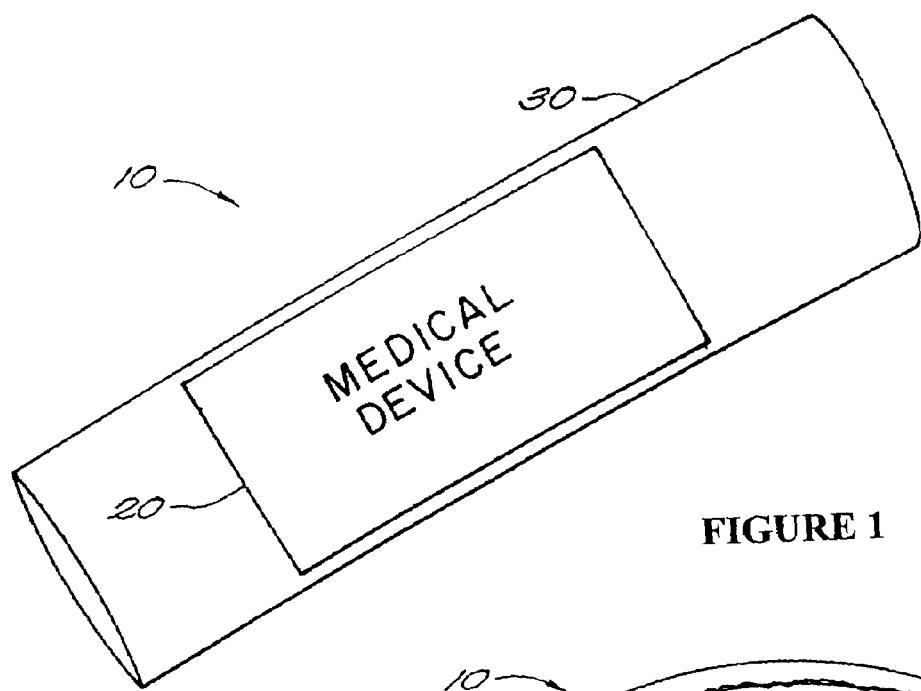
FIG. 1 is a depiction of an example of a tunneling device comprised as a medical device enclosed by a sheath in accordance with an example of the current invention.

FIG. 1 is a depiction of a tunneling device 10 that is comprised in the general case of a medical device 20, surrounded by a sheath 30. Tunneling device 10 is intended for implantation in the body of a patient to perform diagnostic or therapeutic functions. The medical device 20 may be realized as a vascular graft, such as a natural tissue graft, or similar implantable biological device. The sheath 30 is constructed of a flexible, compressive material that protects the medical device during implantation of the device into the tissue of a patient. Sheath 30 may be open at both ends or may be closed at one or both ends.

Figure 2:
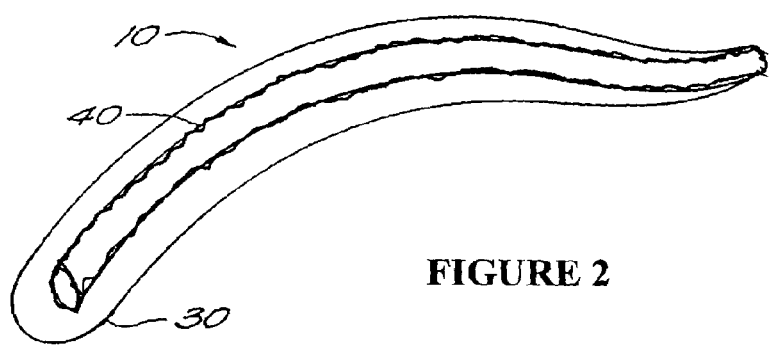
FIG. 2 is a depiction of an example of a tunneling device in the form of a vascular graft enclosed by a sheath.

FIG. 2 shows a tunneling device 10 wherein medical device 20 is realized as a vascular graft 40 enclosed by a sheath 30 that advantageously protects graft 40 during the implantation of the graft. One of ordinary skill in the art will recognize that the current invention is not directed to a specific vascular graft design, but is generically applicable to many different types of vascular grafts which may be a natural tissue graft and/or synthetic graft constructed from different materials. Examples of different synthetic vascular grafts that are contemplated to be within the scope of this invention include, by way of example, the grafts described in the following commonly assigned United States patent applications: U.S. Ser. No. 07/760,753 for "IMPLANTABLE PROSTHETIC DEVICE FOR THE DELIVERY OF A BIOACTIVE MATERIAL"; U.S. Ser. No. 07/760,716 for "MANUALLY SEPARABLE MULTI-LUMEN VASCULAR GRAFT"; U.S. Ser. No. 07/760,728 for "IMPLANTABLE PROSTHETIC DEVICE HAVING INTEGRAL PATENCY DIAGNOSTIC INDICIA"; U.S. Ser. No. 07/760,717 for "POLYLUMENAL IMPLANTABLE ORGAN"; and U.S. Ser. No. 07/760,718 for "SELF-SEALING IMPLANTABLE VASCULAR GRAFT" all of which were filed 16 Sep. 1991. The specifications of these applications for patent are hereby incorporated herein by reference.

While acknowledging that many different types of vascular grafts are suitable to practice the invention, a vascular graft 40 formed of a natural tissue may be used according to an illustrative embodiment of the invention. Although the invention is not so limited, a natural tissue graft may be formed of a vein taken from elsewhere in the patient or another body, such as another person or animal. By way of example, the natural tissue graft may include a saphenous vein, such as the vena saphena magna, vena saphena accessoria, and/or the vena saphena parva.

Referring again to FIG. 2, an example of a sheath 30 is a low-profile cylindrical tube made of a flexible and compressive material that encloses vascular graft 40 along the longitudinal axis of the graft 40 to protect the graft 40 during the implantation process. Sheath 30 is preferably fabricated from polyethylene, and may be open at both ends or closed at one or both of the ends. Sheath 30 is preferably translucent in order to allow observation of the graft 40. Sheath 30 may be sized to have a inside diameter only slightly larger than the outside diameter of the device which it encompasses. The thickness of the cylindrical walls of sheath 30 is approximately 2 to 4 microns. One of ordinary skill in the art will recognize that although polyethylene is described as the preferred material for fabrication of sheath 30, other materials may be used that come within the scope of the invention. These materials include but are not limited to Mylar ribbon, Teflon ribbon, and polypropylene.

Tunneling device 10, represented, in one example, as a vascular graft 40 having an enclosing sheath 30, is designed for insertion within a tunnel cavity, and thus it is advantageous for the tunneling device to have a low coefficient of friction for ease of insertion and subsequent removal of the sheath after implantation of the graft. Sheath 30 may be fixedly attached to vascular graft 40 at one end of the graft. The sheath 30 may be also provided separately, as shown in FIG. 1, and attached to vascular graft 40 by the surgeon, such as, for example, during the grafting process. The sheath 30 may be joined to the vascular graft 40 using simple mechanical means or a compression fit collar or stapled or sutured or other fastening techniques acceptable for implantation within the tissue of the body. The sheath 30 is preferably fabricated from polyethylene. Polyethylene is a soft and ductile material that accommodates the flexibility of vascular graft 40, and when compacted, the coefficient of friction is not appreciatively increased. In one embodiment of the invention, sheath 30 may be coated with a lubricous material to further decrease its coefficient of friction. Sheath 30 may also be coated with hydrophilic materials to facilitate insertion of the device or chemotherapeutic agents for delivery of therapeutic materials.

Figure 3:
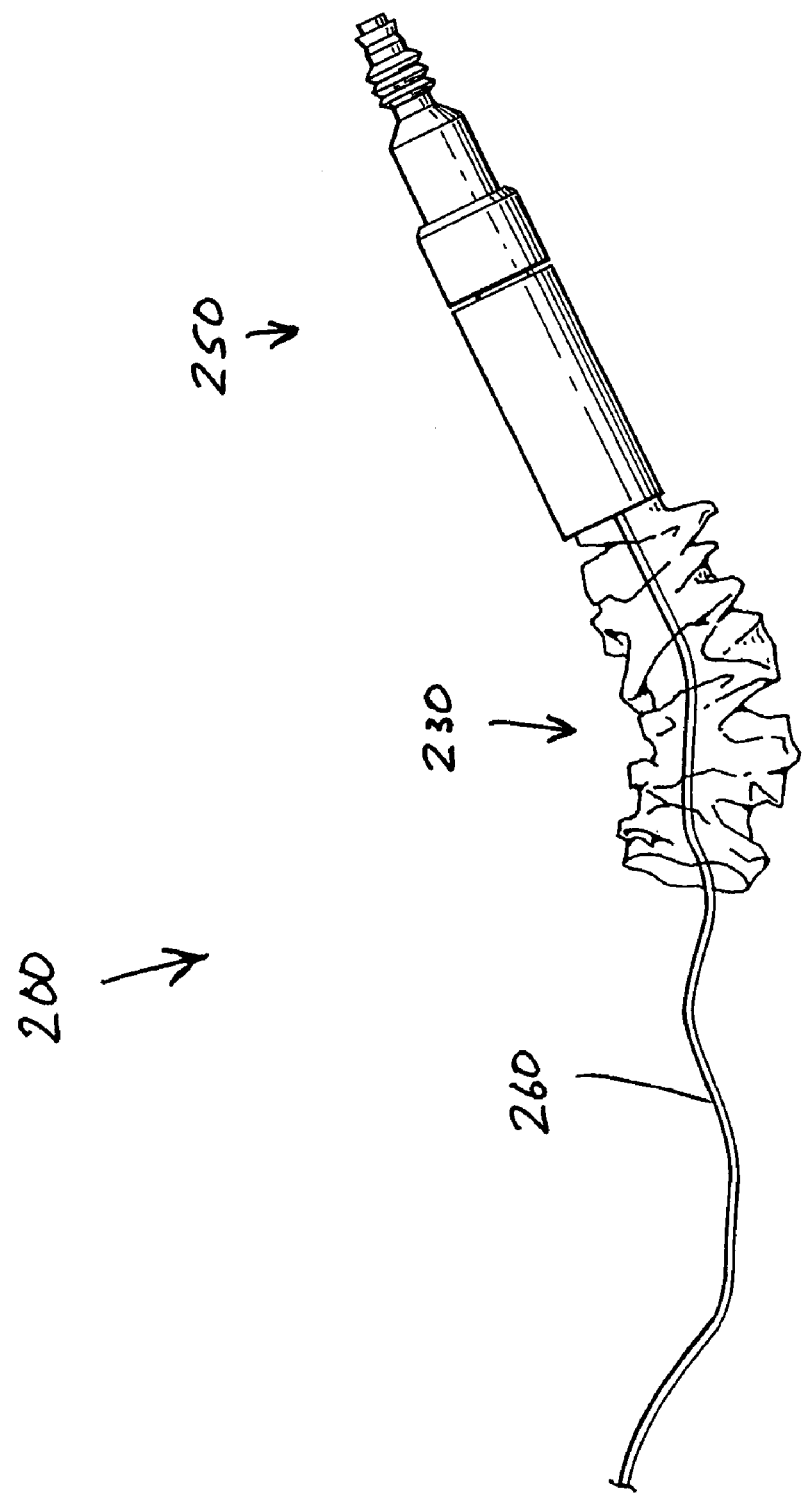
FIG. 3 is a depiction of a tunneling device according to an embodiment of the invention.

FIG. 3 illustrates a tunneling device 200 according to an exemplary embodiment of the current invention. The tunneling device 200 includes a connector 250 for connecting to an end of a tunneler instrument. A sheath 230 is attached to the connector 250. According to this example, a longitudinal coupler 260 is provided as part of the connector 250. At least part of the longitudinal coupler 260 is located in the sheath 230, such as in a lumen defined by the sheath 230. The sheath 230 may be formed of polyethylene, with optional variations and coatings as described herein in relation to sheaths of other embodiments. The longitudinal coupler 260 may be formed of a wide variety of materials. Although the invention is not so limited, examples include a surgical tie, such as a silicone surgical tie, and a suture material. The longitudinal coupler 260 is provided in order to attach a medical device, such as a vascular graft, thereto.

Figure 4:
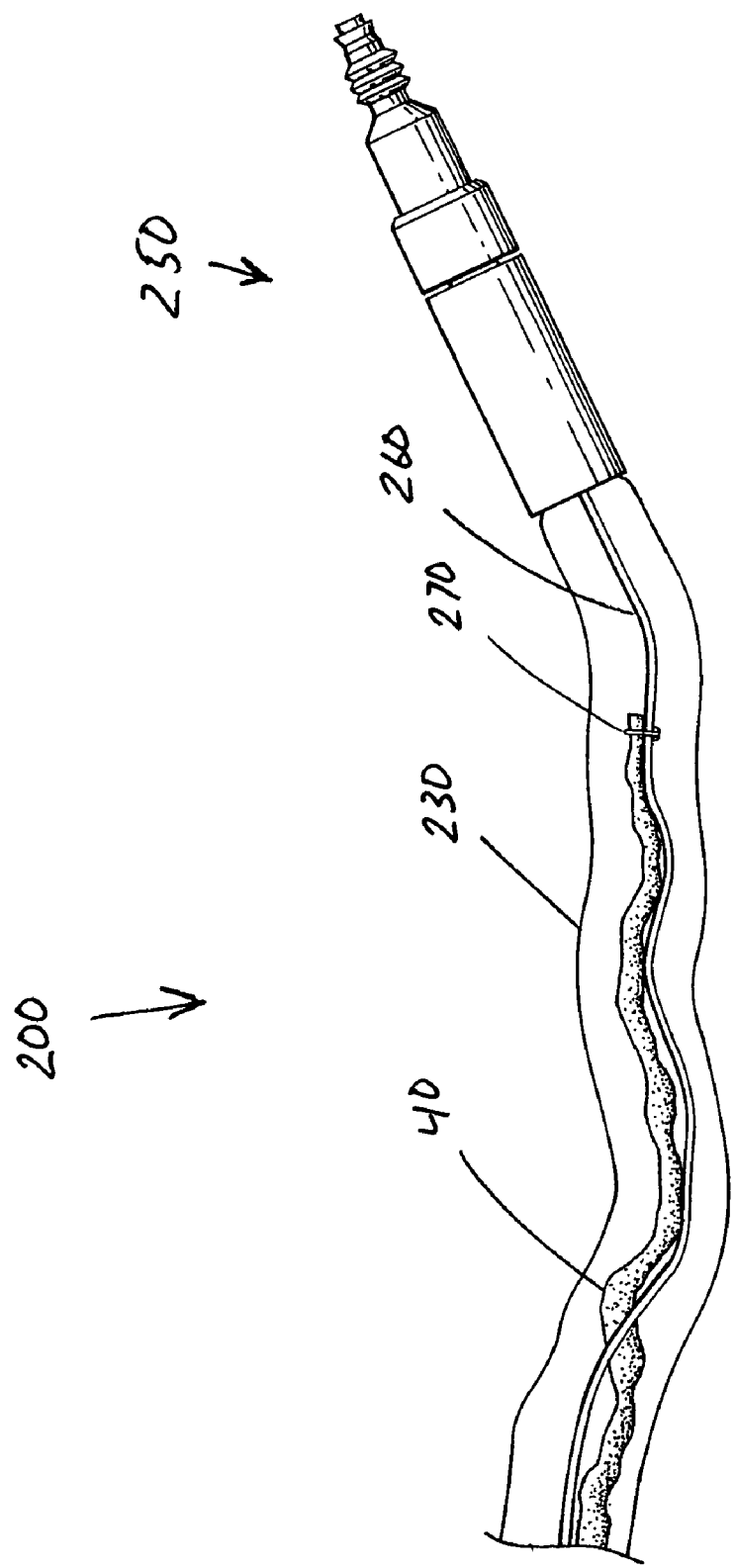
FIG. 4 is a depiction of the tunneling device of FIG. 3 with the sheath in an extended position.

In operation, the tunneling device 200 may be arranged such that a portion of the longitudinal coupler 260 is not enclosed by the sheath 230, such as is shown in FIG. 3 by way of example. With reference to FIG. 4, a graft 40 is attached to the longitudinal coupler 260. Although the invention is not so limited, the graft 40 may be attached to the longitudinal coupler 260 by an attachment device 270, such as one or more surgical clips and/or sutures, for example. The longitudinal coupler 260 may also be attached directly to the graft 40, such as by tying them together. Other methods of attachment may be apparent to one of skill in the art and are to be considered to be within the scope of the invention. It is understood that the graft 40 may be attached to an end of the longitudinal coupler 260, or at any location along the length of the longitudinal coupler 260 as permitted by retraction of the sheath 230 and/or any optional elastic properties of the longitudinal coupler 260 enabling the longitudinal coupler 260 to be extended. It is also understood that the sheath 230 may be retracted in a wide variety of ways. For example, although the invention is not so limited, the sheath 230 could be rolled or folded in an accordion-type of folding, as illustrated. Any extra length of the longitudinal coupler 260 may optionally be removed, if desired.

Figure 5:
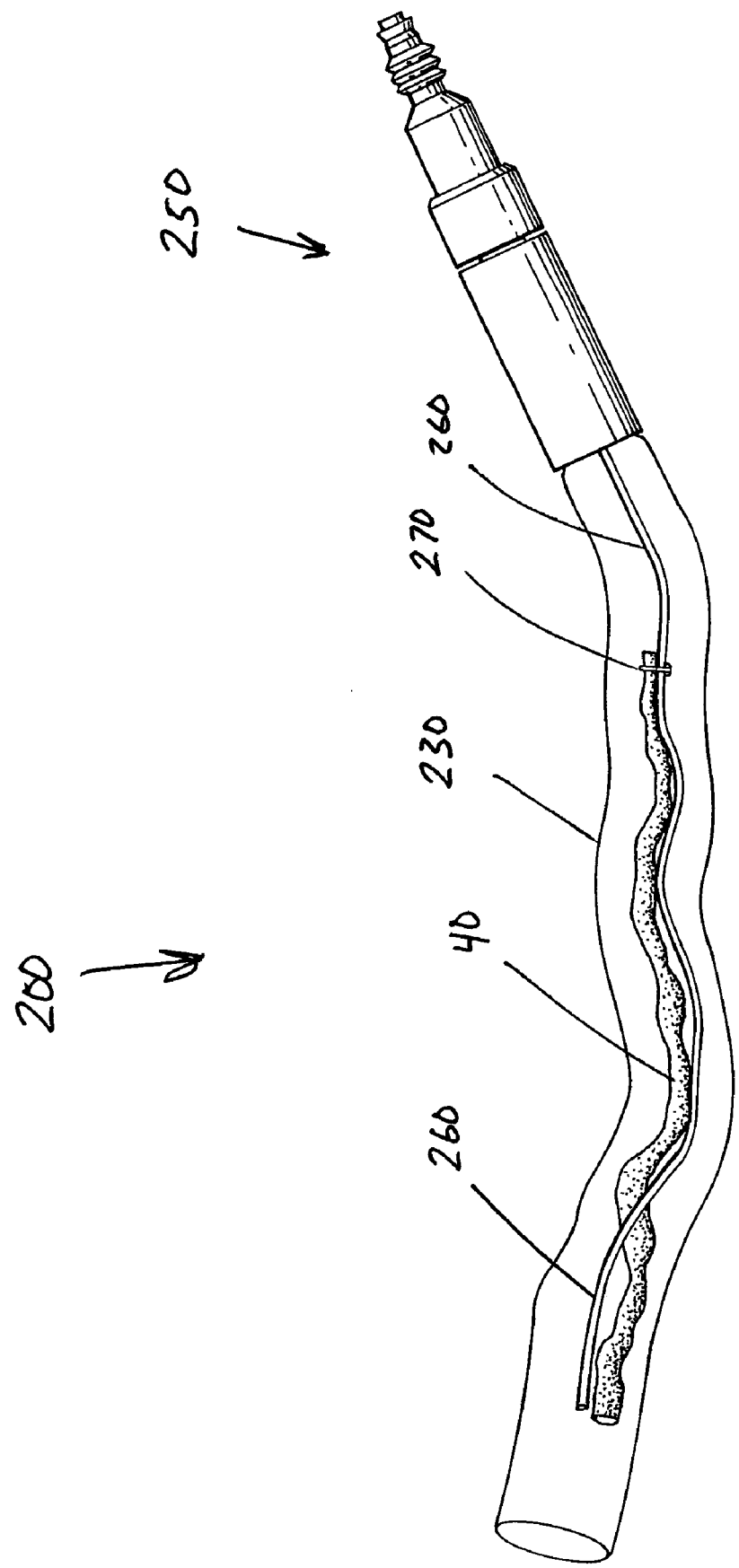
FIG. 5 is a depiction of a further example of a tunneling device according to an implementation of the invention.

The sheath 230 is then extended to cover at least a portion of the length of the graft 40 as is shown by way of example, in FIG. 4. It is understood that the sheath 230 need not be extended to be smooth, as the sheath 230 is suitable for use in a wide variety of conditions. According to an implementation of the invention, the sheath 230 covers the entire length of the graft 40, as shown in FIG. 5. By covering an entire length of the graft 40, positioning of the graft 40, whether a natural tissue graft or a graft formed of other materials, within the body can more easily include movement of the graft 40 in multiple directions, as the sheath 230 is covering both ends of the graft 40.

Figure 6:
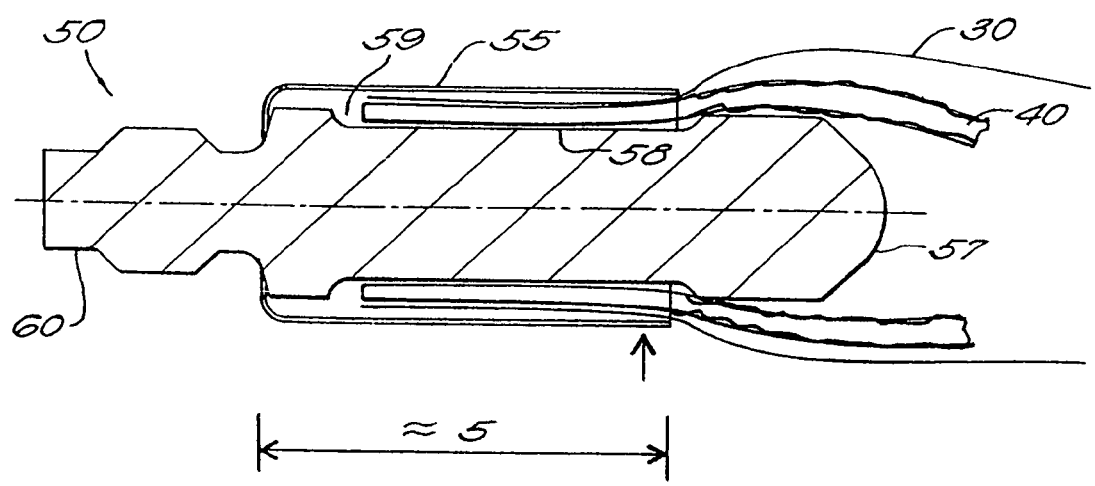
FIGS. 6 and 7 are depictions of further examples of connectors according to implementations of the invention.
Figure 7:
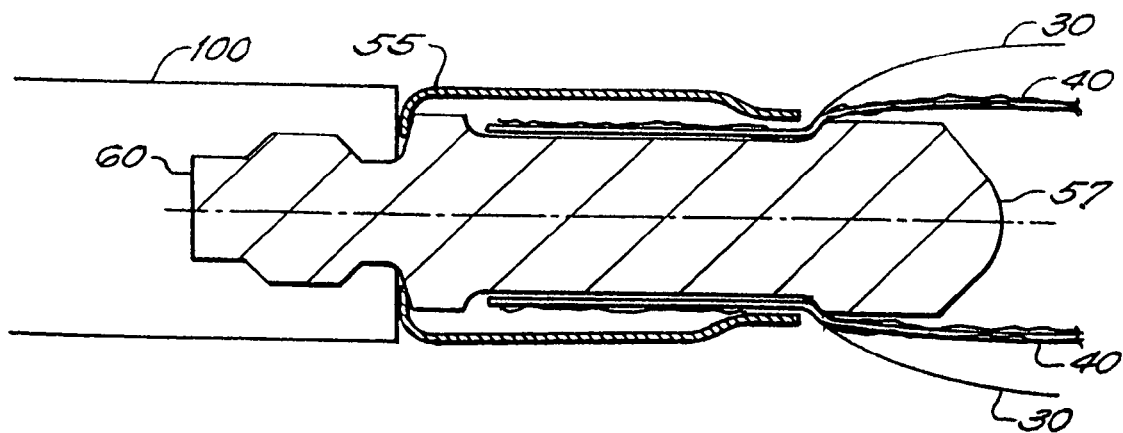

With reference to FIG. 6, in one practice of the invention, a connector 50 includes a cylindrical ferrule 55 that encloses the outer surface of vascular graft 40 at one end of the graft. Ferrule 55 houses a solid core 57 that is generally cylindrical in shape. Core 57 includes a beveled groove 58 around the periphery of core 57 to define an annular channel 59 between core 57 and ferrule 55. Channel 59 defines an annular opening sufficient to accept graft 40 and sheath in the beveled groove 58 between ferrule 55 and core 57. According to one implementation, connector 50 may be coupled to the graft 40 by crimping the ferrule 55 of the tip 50 to core 57, enclosing graft 40 and sheath 30 within channel 59, thus fixedly positioning graft 40 and sheath 30 therein. As shown in FIG. 7, connector 50 can be swaged at the end of ferrule 55 in a recessed fashion to create a substantially seamless connection that does not appreciatively increase the outside diameter of the graft 40 to inhibit plowing of the tissue and further dissection when the graft is pulled through a tunneled passageway.

According to an embodiment of the invention, connector 50 includes an end 60 for attachment of the connector to a tunneler instrument 100. In one practice of the invention, end 60 is a screw mechanism using screw threads for connecting the connector 50 to the tunneler instrument 100. Other conventional methods of fastening the connector to the tunneling instrument include snap-on and/or clip-on techniques that allow the connector 50 to snap and/or clip into a tunneling instrument. These and other fastening techniques are contemplated to be within the scope of the invention.

Figure 8:
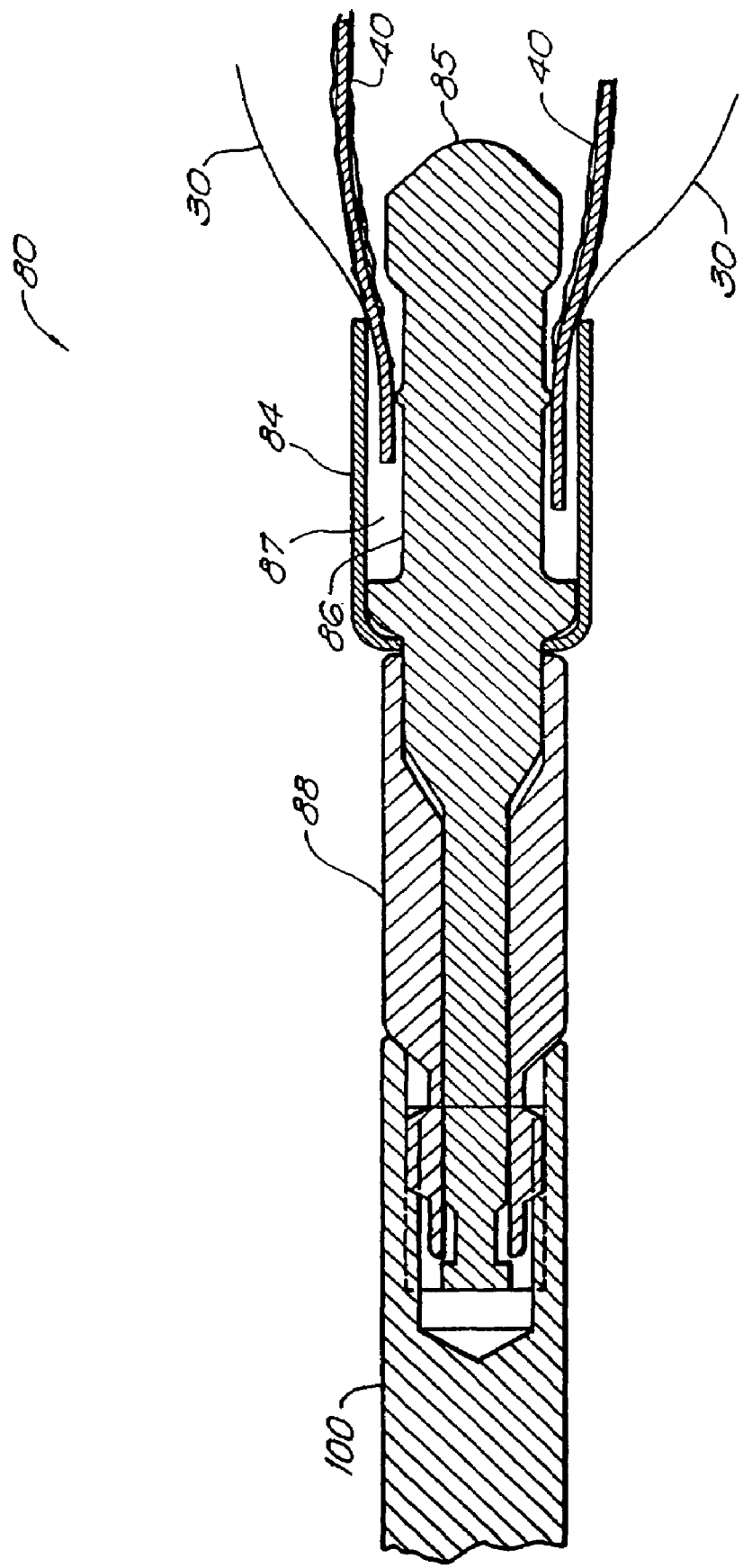
FIG. 8 is a depiction of the a connector having a swivel connector.

In another embodiment as shown in FIG. 8, connector 80 has a swivel mechanism that allows connector 82 to be screwed into the tunneler instrument 100 without rotating the graft and changing the orientation of the tunneling device with the tunneler instrument 100. In this embodiment, connector 80 includes a ferrule 84 that houses a solid core 85 which is generally cylindrical in shape. Core 85 includes a beveled groove 86 around the periphery of core 85 to define an annular channel 87 between core 85 and ferrule 84. Core 85 is coupled to a swivel rod 88 having a distal end for connecting to a tunneler instrument 100. Swivel rod 88 is coupled to core 85 so that swivel rod 88 is rotatable about its longitudinal axis allowing the device to be connected with rotating the graft 40. Channel 87 defines an annular opening sufficient to accept graft 40 and sheath in the beveled groove 86 between ferrule 84 and core 85. Connector 80 may be coupled to the graft 40 by stitching and/or crimping the ferrule 84 of the tip 80 to core 85, enclosing graft 40 and sheath 30 within beveled groove 86, and fixedly positioning graft 40 and sheath 30 therein.

Connector 50 may be constructed of stainless steel, but one of ordinary skill in the art will recognize that other materials may be suitable to connect the graft 40 to the tunneling device. One such example of an alternative material is a plastic, such as a hard plastic.

Figure 9:
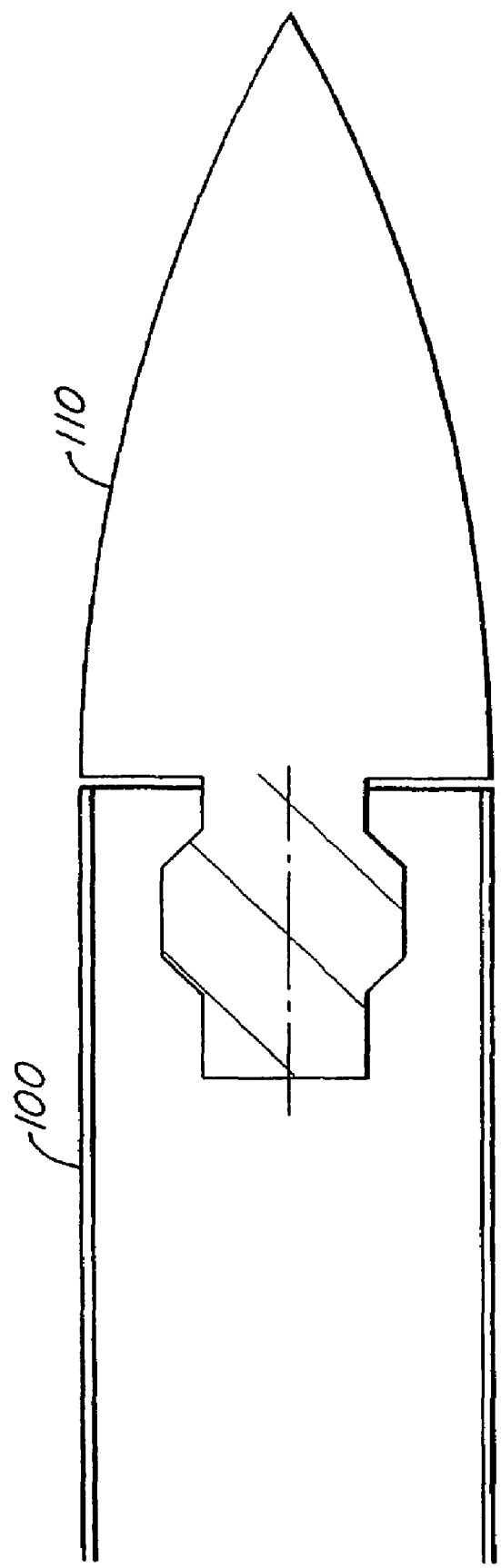
FIG. 9 is a depiction of a tip portion attached to a tunneling instrument.

FIG. 9 illustrates an example of a tip portion 110 connected to the tunneling instrument 100. As illustrated by FIGS. 8 and 10, the tip portion 110 and connector 50 may be interchangeably mountable to the tunneling instrument 100.

According to a further implementation of the invention, a perfusate may be provided in the sheath for communication with the graft. Examples of such a perfusate include, but are not limited to phasphate-buffered saline, saline and buffered saline.

The present invention has been described by way of example, and modifications and variations of the exemplary embodiments will suggest themselves to skilled artisans in this field without departing from the spirit of the invention. Features and characteristics of the above-described embodiments, implementations and examples may be used in combination. The preferred embodiments are merely illustrative and should not be considered restrictive in any way. The scope of the invention is to be measured by the appended claims, rather than the preceding description, and all variations and equivalents that fall within the range of the claims are intended to be embraced therein.

What is claimed is:

1. A tunneling device for subcutaneous deployment by a tunneling instrument, the tunneling device comprising:
   a sheath;
   a connector adapted to couple the tunneling instrument to the sheath;
   wherein the connector includes a longitudinal coupler comprising a surgical tie, a first end of the longitudinal coupler being located within a lumen of the sheath and wherein the longitudinal coupler comprises a flexible material and is adapted to be attached to a graft.

2. The tunneling device of claim 1, wherein the sheath is adapted to be retracted to expose a portion of the longitudinal coupler.

3. The tunneling device of claim 2, wherein the sheath is adapted to be extended to cover an entire length of the graft.

4. The tunneling device of claim 1, wherein the connector includes a surgical clip to secure the graft to the longitudinal coupler.

5. The tunneling device of claim 1, wherein the sheath is composed of at least one of the group consisting of polytetrafluoroethylene, polyethylene, TEFLON, MYLAR, and polypropylene.

6. The tunneling device of claim 1, wherein the connector includes a screw thread formed on a surface thereof to provide the sutureless connection of the graft to the tunneling instrument.

7. The tunneling device of claim 1, wherein the connector enables rotation of the graft relative to the tunneling instrument to facilitate attachment of the graft to the tunneling instrument.

8. The tunneling device of claim 1, wherein the sheath is coated with at least one of the group consisting of a lubricous material, a hydrophilic material, and a chemotherapeutic agent.

9. The tunneling device of claim 1, further comprising a perfusate located within the sheath and in communication with the graft.

10. The tunneling device of claim 1, wherein the connector further comprises:
   a core having a grooved formed therein, and
   a cylindrical ferrule positioned about the groove, a portion of the sheath and the longitudinal coupler being positioned between the ferrule and the core within the groove, the ferrule being crimped about the core to fix the sheath and the longitudinal coupler to the connector.

11. The tunneling device of claim 1, wherein the longitudinal coupler is adapted to be attached to a synthetic vascular graft.

12. The tunneling device of claim 1, wherein the longitudinal coupler is adapted to be attached to a natural tissue vascular graft.

13. The tunneling device of claim 12, wherein the natural tissue vascular graft is selected from the group of: vena saphena magna, vena saphena accessoria, and/or the vena saphena parva.

14. A tunneling device for subcutaneous deployment by a tunneling instrument, the tunneling device comprising:
a sheath;
a connector adapted to couple the tunneling instrument to the sheath;
wherein the connector includes a longitudinal coupler and a suture to secure a graft to the longitudinal coupler, a first end of the longitudinal coupler being located within a lumen of the sheath and wherein the longitudinal coupler comprises a flexible material.

* * * * *